United States Patent [19]  [11]  4,140,848
Myers  [45]  Feb. 20, 1979

[54] AMINO DERIVATIVES OF 4"-DEOXY-OLEANDOMYCIN

[75] Inventor: Robert F. Myers, East Lyme, Conn.

[73] Assignee: Pfizer Inc., New York, N.Y.

[21] Appl. No.: 870,160

[22] Filed: Jan. 17, 1978

Related U.S. Application Data

[62] Division of Ser. No. 765,488, Feb. 4, 1977, Pat. No. 4,085,119.

[51] Int. Cl.$^2$ .................. C07H 17/08; A01N 9/00
[52] U.S. Cl. ....................... 536/9; 424/180; 536/17
[58] Field of Search ......................... 536/9, 17

[56] References Cited

U.S. PATENT DOCUMENTS

| | | | |
|---|---|---|---|
| 3,963,696 | 6/1976 | Martin et al. | 536/9 |
| 4,036,853 | 7/1977 | Sciavolino | 536/9 |

Primary Examiner—Johnnie R. Brown
Assistant Examiner—Blondel Hazel
Attorney, Agent, or Firm—Francis X. Murphy; Charles J. Knuth; Albert E. Frost

[57] ABSTRACT

Derivatives of oleandomycin, its 11-monoalkanoyl and 11,2'-dialkanoyl esters having at the 4"-position an amino group substituted with a group having the formula —$(CH_2)_n$—Z—R wherein n is an integer from 2 to 4 when Z is O, S, SO, $SO_2$ or NH, and n is an integer from 1 to 4 when Z is CO or CHOH, and R is a phenyl, substituted phenyl or a heterocyclyl group, their preparation, and use as antibacterial agents is described.

8 Claims, No Drawings

AMINO DERIVATIVES OF 4''-DEOXY-OLEANDOMYCIN

CROSS REFERENCE TO RELATED APPLICATION

This application is a division of application Ser. No. 765,488 filed Feb. 4, 1977, now U.S. Pat. No. 4,085,119.

BACKGROUND OF THE INVENTION

1. Field of the Invention

This invention relates to a structurally unique group of macrolides and, more particularly, to derivatives of oleandomycin, its 11-mono- and 11,2'-dialkanoyl esters having at the 4''-position an amino group substituted with an alkylene group having from 1 to 4 carbon atoms and at its end position a group of the formula —Z—R wherein Z is O, S, SO, $SO_2$, <CO, CHOH or NH; and R is a phenyl, substituted phenyl, pyridyl, 2-pyrimidinyl, 2-(1-methyl)imidazolyl or chloro substituted pyridyl group, and to methods for their preparation. The compounds are antibacterial agents.

2. Description of the Prior Art

Oleandomycin, a macrolide antibiotic produced by fermentation, was first described in U.S. Pat. No. 2,757,123. It has the formula, the absolute configuration of which is shown below:

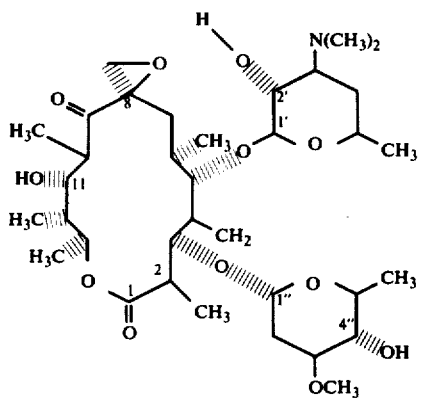

It consists of three main structural features: the L-oleandrose moiety, the desosamine moiety and the oleandolide moiety.

Derivatization of oleandomycin has focused primarily upon the formation of esters at one or more of three hydroxy groups located at the 2', 4'', and 11-positions. Mono-, di- and triacyl esters wherein the acyl moiety is derived from a lower aliphatic hydrocarbon monocarboxylic acid having from two to six carbon atoms are described in U.S. Pat. No. 3,022,219.

Aminohydrin derivatives of oleandomycin are reported by Kastrons et al., *Khim. Geterosikl Soedin* (2), 168–71 (1974); C.A. 80, 145986n (1974). The compounds, for which no utility is reported, are prepared by treating oleandomycin with a dialkylamine or a heterocyclic amine in a sealed tube for twenty hours at 30° C. The epoxide moiety at the 8-position is the site of reaction.

SUMMARY OF THE INVENTION

There has now been found a series of oleandomycin derivatives each of which exhibits valuable antibacterial activity in vitro and many of which exhibit in vivo activity by the parenteral and oral routes of administration, particularly against Gram-positive microorganisms. The compounds of this invention have formula II below wherein the wavy line connecting the substituted amino group at the 4''-position is generic to and embracive of both epimeric forms:

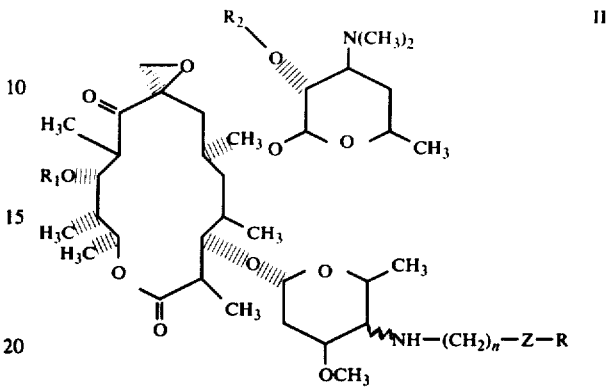

wherein each of $R_1$ and $R_2$ is selected from the group consisting of hydrogen, and alkanoyl having from two to three carbon atoms (acetyl and propionyl); n is an integer from 1 to 4; Z is selected from the group consisting of O, S, SO, $SO_2$, <CO, CHOH and NH; provided that when Z is O, S, SO, $SO_2$ or NH, n is an integer from 2 to 4, and when Z is CO or CHOH, n is an integer from 1 to 4; and R is selected from the group consisting of a first subgroup consisting of

and a second subgroup consisting of heterocyclyl; wherein X is selected from the group consisting of hydrogen, chloro, bromo, fluoro, alkyl having from one to four carbon atoms, alkoxy having from one to four carbon atoms, trifluoromethyl, $N(CH_3)_2$, cyano, thioalkyl having from one to four carbon atoms and sulfonylalkyl having from one to four carbon atoms; and heterocyclyl is selected from the group consisting of pyridyl, chloro substituted pyridyl, 2-pyrimidinyl and 2-(1-methyl)imidazolyl.

Also included in the present invention are the pharmaceutically acceptable salts of compounds of formula II above. Representative of such salts, but not limited thereto, are the hydrochloride, hydrobromide, phosphate, sulfate, formate, acetate, propionate, butyrate, citrate, glycolate, lactate, tartrate, malate, maleate, fumarate, gluconate, stearate, mandelate, pamoate, benzoate, succinate, lactate, p-toluenesulfonate, and aspartate.

Favored because of their greater in vivo activity relative to that of other compounds described herein are compounds of formula II wherein $R_1$ is acetyl, $R_2$ is hydrogen, and —$(CH_2)_n$—Z—R has the values shown below:

| n | Z | R |
|---|----|---|
| 2 | NH | first subgroup |

-continued

| n | Z | R | |
|---|---|---|---|
| 1 | CHOH | first subgroup |  |
| 2 | S | second subgroup | pyridyl |
| 2 | O | second subgroup | pyridyl |
| 2 | S | second subgroup | 2-pyrimidyl |

Preferred compounds because of their greater oral activity relative to that of other compounds described herein are those compounds wherein $R_1$ is acetyl, $R_2$ is hydrogen and $(CH_2)_n$—Z—R has the values shown below:

| n | Z | R | |
|---|---|---|---|
| 2 | NH | first subgroup | $C_6H_5$ |
| 1 | CHOH | first subgroup | $C_6H_5$ |
| 2 | S | second subgroup | 2-pyridyl |
| 2 | S | second subgroup | 4-pyridyl |
| 2 | S | second subgroup | 2-pyrimidinyl |
| 2 | O | second subgroup | 2-pyridyl |

Compounds of formula II, including the epimeric forms thereof, and their pharmaceutically acceptable salts are effective antibacterial agents against Gram-positive microorganisms, e.g. *Staphylococcus aureus* and *Streptococcus pyogenes,* in vitro and many are active in vivo via the parenteral and oral routes of administration. Many of the compounds (and their salts) are also active against certain Gram-negative microorganisms, such as cocci, e.g. *Pasteurella multocida* and *Neisseria sicca.*

DETAILED DESCRIPTION OF THE INVENTION

The structurally unique oleandomycin derivatives of this invention of formula II are prepared by reaction of the appropriate ketone of formula III:

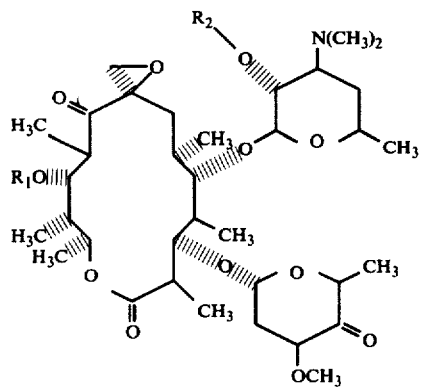

III wherein each of $R_1$ and $R_2$ is as previously defined, with the appropriate amine [$H_2N$—$(CH_2)_n$—Z—R] reactant wherein n, Z and R are as defined above, in a reaction-inert solvent to form an intermediate Schiff base compound which is then reduced to the corresponding substituted amino derivative. Alternatively, rather than conduct the process in this stepwise fashion, the overall process, a reductive amination, can be carried out by reacting a formula III compound and an appropriate amine [$H_2N$—$(CH_2)_n$—Z—R] in the presence of a suitable reducing agent. The reaction when conducted in this manner is considered a one-step process since all reactants are added simultaneously, or both the ketone reactant and reducing agent are added simultaneously to the amine reactant, or the amine reactant and reducing agent are added simultaneously to the ketone. Regardless of the manner in which the reaction is carried out, the overall reaction is a reductive amination of the ketone (formula III) as previously noted. Since the amine reactant and reducing agent are more readily available than are the ketone compounds of formula III, it is preferred to carry out the reaction in a stepwise manner to first form the intermediate Schiff base which is then reduced. The Schiff base intermediate need not be isolated. An inert atmosphere can be used but is not required. Regardless of the manner in which it is carried out, the process is generally conducted in a reaction-inert solvent; i.e., one which does not react with reactants or products.

The molar ratio of ketone compound to amine reactant can vary widely, e.g., from about 1:1 to about 1:10. Molar ratios of less than 1:1 are avoided for economic reasons to insure maximum reaction of the ketone compound, normally the least available of the reactants. Ratios of greater than 1:10 are seldom used since they do not appear to improve the yield of final product.

Suitable reaction-inert solvents are alcohols having from one to four carbon atoms, ethylene glycol, propylene glycol, tetrahydrofuran, dioxane, diethyl ether, benzene, toluene, acetonitrile, methylene chloride. The favored solvents are polar solvents such as alcohols and acetonitrile which afford a faster rate of reaction relative to that of non-polar solvents. When using a 2'-alkanoyl or an 11,2'-dialkanoyl derivative of formula III or IV as reactant, a secondary alcohol, and preferably isopropanol, is used as solvent to avoid removal of the 2'-alkanoyl group; unless, of course, removal of such group is desired.

The reaction can be carried out at temperatures from about −10° C. to about 50° C. The temperature range of from about 10° C. to about 30° C. is favored since it permits a satisfactory rate of reaction and satisfactory yields of product.

The reaction between the ketone and amine reactant is acid-catalyzed. For convenience, the amine reactant is used as the free base form and the appropriate acid added to form the acid addition salt in situ. Alternatively, the amine reactant can be used in the form of an acid addition salt with an organic or inorganic acid, e.g., acetic, butyric, formic, hydrochloric, hydrobromic, hydriodic, sulfuric, nitric or phosphoric acid. The acetate and hydrochloride salts are the favored acid addition salts primarily because of their availability. The presence of the acid tends to accelerate Schiff base formation and to increase the yield of desired product. The molar ratio of acid to amine reactant used is desirably in the range of from about 0.5:1.0 to 1.5:1. At ratios outside these ranges, the yield of the final product is reduced. Best results are generally achieved with equimolar or approximately equimolar proportions (e.g., 0.8:1 to 1.2:1) of acid to amine reactant.

An alternative method for preparing compounds of this invention comprises condensation of the appropriate aldehyde R—Z—$(CH_2)_{n-1}$—CHO wherein n, Z and R are as defined above with the appropriate amine reactant of formula IV:

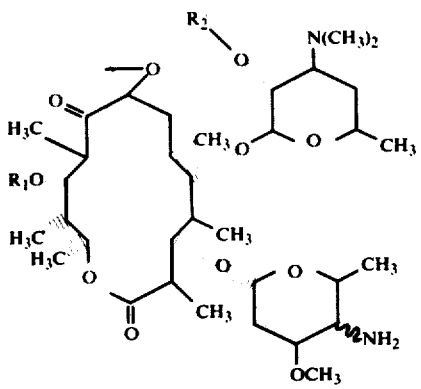

in a reaction-inert solvent at a temperature of from about −10° C. to about 50° C. The reaction mixture thus produced, which is believed to contain a Schiff base, is then treated with a reducing agent to produce the desired product having formula II. This process is conducted under essentially the same conditions as are recited above for the first method. The only parameter in which a difference exists, and this only a minor difference, is the temperature range. The second method appears to permit a somewhat lower range as the preferred range; namely, from about −10° C. to 10° C.

The reaction of this method is also acid catalyzed. The amine reactant of formula IV can be in the form of an acid addition salt with any of a variety of acids, such as a strong mineral acid, e.g., hydrochloric, hydrobromic, hydriodic, sulfuric, nitric or phosphoric acid; an alkanoic acid having from one to four carbon atoms, e.g., formic, acetic, propionic or butyric acids. Alternatively, said amine reactant can be used as the free base form and an appropriate acid added to form the acid addition salt in situ. The acetate and hydrochloride salts are the favored acid addition salts primarily because of their availability. The presence of the acid addition salt form of the amine reactant tends to accelerate Schiff base formation and to increase the yield of desired product. The molar ratio of acid to amine reactant used is desirably in the range of from about 0.5:1.0 to 1.5:1. At ratios outside these ranges, the yield of the final product is reduced. Best results are generally achieved with equimolar or approximately equimolar proportions (e.g., 0.8:1 to 1.2:1) of acid to amine reactant.

While in principle a variety of reducing agents can be used in either method to achieve the overall reaction of reductive amination, in practice care must be exercised in the choice of reducing agents because of the presence of other reducible groups in the ketone reactant (formula III) or amine reactant (formula IV).

The favored reducing agent is sodium cyanoborohydride since it effectively accomplishes only the desired reduction and requires relatively mild conditions. Further, it is not affected by by-product water present in the reaction mixture. It is used in ratios of from about one to about three equivalents per mole of ketone reactant of formula III or of formula R—Z—(CH$_2$)$_{n−1}$—CHO.

Other reducing agents which can be used are hydrogen in the presence of palladium-on-charcoal and borane-dimethylamine complex.

The above-described processes generate water which need not be removed from the reaction mixtures. However, if desired, the by-product water can be removed by conducting the reaction at reduced pressure or by "effectively" removing it by the use of molecular sieves as adsorbent for the water. Suitable adsorbents are the natural and synthetic crystalline aluminosilicates. The latter adsorbents are favored because of their greater water-loading capacity relative to the natural crystalline aluminosilicates. Included among such adsorbents are chabazite, a naturally occurring material, the synthetic "Linde Molecular Sieves" produced and distributed by the Linde Company, such as Types 4A, 5A and 13X, and the "Microtraps" produced by the Davison Chemical Company. Such materials sorb and thus effectively remove water from the reaction medium. The exhausted or partially exhausted aluminosilicate is separated from the reaction mixture by filtration or decantation.

When using a molecular sieve to effectively remove by-product water, it is necessary to use a reaction-inert solvent such as benzene, toluene, dimethyl sulfoxide, ethanol or propanol. Atmospheric pressure is favored for reasons of simplicity of equipment and ease of operation although sub- or superatmospheric pressures can be used if desired. The quantity of molecular sieve to be used depends upon the reaction conditions such as temperature, solvent, and on the nature of the molecular sieve itself and is best determined by experiment. In general, however, a quantity sufficient to sorb the theoretical amount of by-product water should be used. In actual practice an excess of molecular sieve is advantageous since it assures more complete reaction.

The reaction mixture, free of molecular sieve, is then reduced as described above.

A further method for preparing compounds of this invention wherein Z is CO and n is 1 comprises alkylation of the appropriate amine reactant of formula IV with an appropriate bromo (or chloro) reactant of the formula BrCH$_2$—CO—R. The reaction is carried out in the presence of an acid acceptor, i.e. an organic base such as a trialkylamine having from 3 to 12 carbon atoms and preferably the readily available triethylamine, in a reaction-inert solvent such as tetrahydrofuran, dioxane, ether, benzene, toluene and methylene chloride. The reactants, formula IV compounds and bromo (or chloro) compound, are reacted in a molar ratio of from 1:1 to 1:2 and desirably in a 1:1 to 1:1.5 ratio. The acid acceptor and bromo (or chloro) reactant are used in equimolar proportions.

The reaction is conducted at a temperature of from about 20° C. to 50° C. Higher temperatures can be used but offer no advantage. Lower temperatures are generally not used because the reaction then requires longer reaction times.

When the formula III reactant is an 11-monoalkanoyl or 11-hydroxyderivative, the reaction produces a mixture of epimers (represented by a wavy line in formula II compounds) which can be separated, if desired. Column chromatography of a chloroform solution of the crude product on silica gel and elution with appropriate solvents, e.g. chloroform-3% methanol, offers a convenient method for separating the epimers. In the present description and illustrations, it is understood that although the compounds are listed as 4″-substituted amino derivatives, both epimers and mixtures thereof are included.

Diester compounds of formula II, i.e. each of $R_1$ and $R_2$ is alkanoyl, can also be prepared by acylation of the corresponding 11-monoalkanoyl ($R_1$ = alkanoyl; $R_2$ =

H) compound by standard procedures known to those skilled in the art, and as exemplified herein. In this manner, preparation of diester compounds wherein the ester groups differ is readily achieved.

Acid addition salts of the compounds of this invention are readily prepared by treating formula II compounds with an equimolar amount of the appropriate acid in a reaction-inert solvent for the formula II compound. The acid addition salts are recovered by filtration if they are insoluble in the reaction-inert solvent, by precipitation, by addition of a non-solvent for said salt, or by evaporation of the solvent.

The 11-mono-alkanoyl- and 11,2'-dialkanoyl-4''-deoxy-4''-oxo-oleandomycin reactants (formula III) are prepared by oxidation of the appropriate 11,2'-dialkanoyl-oleandomycin with, for example, N-chlorosuccinimide-dimethyl sulfide, to the corresponding 11,2'-dialkanoyl-4''-deoxy-4''-oxo-oleandomycin. Solvolysis of the diester by treatment with methanol affords the 11-monoester product. In like manner, 4''-deoxy-4''-oxo-oleandomycin is prepared from 2'-alkanoyl-oleandomycin by oxidation and hydrolysis.

The 11-mono-alkanoyl- and 11,2'-dialkanoyl-4''-deoxy-4''-amino-oleandomycin reactants (formula IV) are prepared by reductive amination of the corresponding 11-mono-alkanoyl-, 2'-monoalkanoyl- and 11,2'-dialkanoyl-4''-deoxy-4''-oxo-oleandomycins using palladium-on-charcoal, hydrogen and ammonium acetate in a suitable solvent, ($CH_3OH$, i—$C_3H_7OH$). Alternatively, sodium cyanoborohydride can be used as reducing agent in place of palladium-on-charcoal and hydrogen. The de-esterified derivative is conveniently prepared by hydrolysis of the corresponding 2'-monoalkanoyl-4''-deoxy-4''-amino-oleandomycins.

The novel oleandomycin derivatives described herein exhibit in vitro activity against a variety of Gram-positive microorganisms and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sickroom utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive and certain Gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated four, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 1 mg./kg. to about 200 mg./kg. of body weight per day. The favored dosage range is from about 5 mg./kg. to about 100 mg./kg. of body weight per pay and the preferred range from about 5 mg./kg. to about 50 mg./kg. of body weight per day. Vehicles suitable for parenteral injection may be either aqueous such as water, isotonic saline, isotonic dextrose, Ringer's solution, or nonaqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable phamacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The requisite starting materials having the formulae $H_2N$—$(CH_2)_n$—Z—R and R—Z—$(CH_2)_{n-1}$—CHO are known materials or are prepared by methods familiar to those skilled in the art, such as are illustrated herein in Preparations G and J.

In the Examples presented herein, no effort was made to recover the maximum amount of product produced or to optimize the yield of a given product. The Examples are merely illustrative of the process and of the products obtainable thereby.

EXAMPLE 1

11-Acetyl-4''-deoxy-4''-(2-hydroxy-2-phenylethyl)amino-oleandomycin

Under nitrogen, a solution of 2-hydroxy-2-phenylethylamine (2.12 g., 15.5 mmol.), acetic acid (0.98 g., 15.4 mmol.) and 11-acetyl-4''-deoxy-4''-oxo-oleandomycin (4.5 g., 6.19 mmol.) in methanol (35 ml.) is cooled in an ice bath and stirred for fifteen minutes. It is then treated dropwise with sodium cyanoborohydride (0.33 g. [of 85%], 4.52 mmol.) in methanol (15 ml.) over a period of 0.5 hours. The ice bath is removed and the reaction mixture stirred for 16 hours. It is then poured into a mixture of diethyl ether (150 ml.) and water (150 ml.).

The aqueous solution is extracted with ether (150 ml.) at each of pH values of 4, 5, 6, 7, 8 and 9.3. The extracts obtained at pH 8 and 9.3 are combined and concentrated under reduced pressure to give 3.0 g. of a white foam.

The foam is dissolved in chloroform (20 ml.) and chromatographed on silica gel (200 g.) using chloroform-5% methanol as eluant. Fractions containing the product are combined and concentrated under reduced pressure to give the title product (430 mg., 7.8%) as a pure white foam. It is a mixture of epimeric products.

Mass Spec. m/e = 264.

NMR (60 MHz) $\delta_{CDCl_3}^{TMS}$ (ppm) 7.4 (s, 5H), 3.40 (s, 3H), 2.66 (s, 2H), 2.30 (s, 6H), 2.06 (s, 3H).

EXAMPLE 2

11-Acetyl-4"-deoxy-4"-[2-(4-pyridyl)thioethyl]amino-oleandomycin

Under an atmosphere of nitrogen, a mixture of 11-acetyl-4"-deoxy-4"-amino-oleandomycin (2.1 g., 2.9 mmol.), acetic acid (0.13 g., 2.9 mmol.) and crude 2-(4-pyridyl)thioacetaldehyde hydrate.HCl (1.97 g., 11.5 mmol.) in methanol (10 ml.) is cooled to −10° C. and stirred for fifteen minutes. Sodium cyanoborohydride (0.155 g. [of 85%], 2.1 mmol.) in methanol (10 ml.) is added and the resulting mixture stirred for one hour below 15° C. and then for 1.75 hours at room temperature. The reaction mixture is then poured into a mixture of diethyl ether (150 ml.) and water (150 ml.). The mixture is extracted with ether (150 ml.) at each of pH values of 4, 5.5, 7, 8, 9 and 10. The extracts from the pH 7, 8 and 9 extractions are combined and concentrated under reduced pressure to give 1.98 g. of a yellow foam which is purified by column chromatography on silica gel (200 g.) using chloroform-5% methanol as eluant to give, after concentration of eluate under reduced pressure, 0.56 g. (22%) of the title product as a mixture of epimers.

Mass spec. m/e = 281.

NMR (60 MHz) $\delta_{CDCl_3}^{TMS}$ (ppm): 8.3–8.5 (broad d, 2H), 7.0–7.3 (broad d, 2H), 3.33 (s, 3H), 2.66 (s, 2H), 2.33 (s, 6H), 2.06 (s, 3H).

EXAMPLE 3

11-Acetyl-4"-deoxy-4"-(benzoylmethyl)amino-oleandomycin

To a solution of triethylamine (0.2 ml.) and 11-acetyl-4"-deoxy-4"-amino oleandomycin (2.0 g., 2.7 mmol.) in tetrahydrofuran (15 ml.) is added α-bromoacetophenone (0.6 g., 3 mmol.) and the mixture stirred at room temperature for 3 hours. The reaction mixture is filtered and the filtrate poured into a mixture of ether (150 ml.) and water (150 ml.) and extracted with diethyl ether at pH levels of 4, 5.5, 7 and 8.5. The extracts from the pH 5.5, 7 and 8.5 extractions are combined and concentrated to give 1.65 g. of a foam. It is purified by chromatography on silica gel (140 g.) using chloroform-5% methanol as eluant. Concentration of the eluate under reduced pressure gives the title product as a white foam (0.5 g., 21.8%), a mixture of epimers.

Mass spec. m/e = 262.

NMR (60 MHz) $\delta_{CDCl_3}^{TMS}$ (ppm): 7.0–8.0 (m, 5H), 3.31 (s, 3H), 2.65 (d, J=2, 2H), 2.30 (s, 6H), 2.05 (s, 3H).

In like manner, the following compounds are prepared from appropriate reactants of formula IV and appropriate bromoacetophenones of the formula

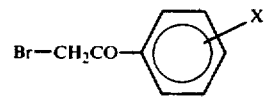

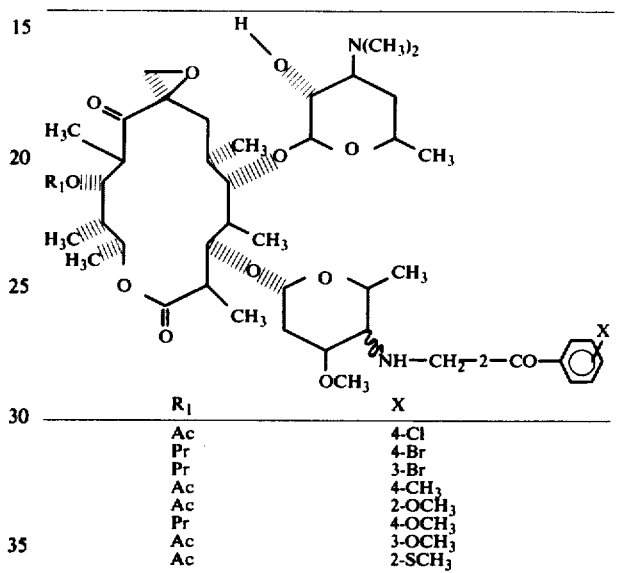

| R₁ | X |
|---|---|
| Ac | 4-Cl |
| Pr | 4-Br |
| Pr | 3-Br |
| Ac | 4-CH₃ |
| Ac | 2-OCH₃ |
| Pr | 4-OCH₃ |
| Ac | 3-OCH₃ |
| Ac | 2-SCH₃ |

Ac = acetyl;
Pr = propionyl

EXAMPLES 4–17

The following compounds are prepared from appropriate reactants by the procedures of Examples 1 or 2 as indicated. In each instance a mixture of epimeric products is obtained.

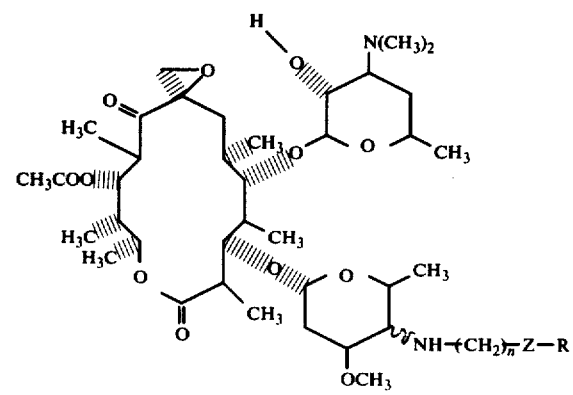

| Example | n | Z | R | Mass Spec. m/e | NMR (60 MHz) $\delta_{CDCL_3}^{TMS}$ (ppm) | Procedure | % Yield |
|---|---|---|---|---|---|---|---|
| 4 | 2 | S | C₆H₅ | | 7.40(s,5H), 3.45(s,3H), 2.78(d,J=2,2H), 2.45(s,6H), 2.2(s,3H). | 2 | 70 |
| 5 | 2 | SO | C₆H₅ | | 7.5(broad s,5H), 3.33(s,3H), 2.65(s,2H), 2.31(s,6H), | 2 | 75 |

-continued

| Example | n | Z | R | Mass Spec. m/e | NMR (60 MHz) $\delta_{CDCL_3}^{TMS}$ (ppm) | Procedure | % Yield |
|---|---|---|---|---|---|---|---|
| 6 | 2 | $SO_2$ | $C_6H_5$ | | 7.4–8.1(m,5H), 3.28(s,3H), 2.66(s,2H), 2.43(s,6H), 2.06(s,3H), 2.03(s,3H). | 2 | 30 |
| 7 | 1 | CHOH | $C_6H_5$ | 264 | 7.4(s,5H), 3.40(s,3H), 2.66(s,2H), 2.30(s,6H), 2.06 (s,3H). | 1 | 8 |
| 8 | 2 | CO | $C_6H_5$ | 275 | 7.0–8.0(m,5H), 3.43(s,3H), 2.70(s,2H), 2.38(s,6H), 2.06 (s,3H). | 2 | 15 |
| 9 | 2 | O | $C_6H_5$ | | 6.9–7.5(m,5H), 3.37(s,3H), 2.66(d,J=2,2H), 2.30 (s,6H), 2.06(s,3H). | 2 | 32 |
| 10 | 2 | NH | $C_6H_5$ | 263 | 6.5–7.4(m,5H), 33.3(s,3H), 2.63(s,2H), 2.26(s,6H), 2.03(s,3H). | 1 | 11 |
| 11 | 2 | S | 2-pyridyl | | 8.2–8.4(m,1H), 6.9–7.5(m,3H), 3.31(s,3H), 2.65(d, J=2,2H), 2.28(s,6H), 2.03(s,3H). | 2 | 10 |
| 12 | 2 | O | 2-pyridyl | 265 | 6.6–8.2(m,4H), 3.31(s,3H), 2.68(d,J=2,2H), 2.33(s, 6H), 2.05(s,3H). | 2 | 49 |
| 13 | 2 | S | 4-pyridyl | 281 | 8.3–8.5(broad d,2H), 7.0–7.3(broad d,2H), 3.33(s,3H), 2.66(s,2H), 2.33(s,6H), 2.06(s,3H). | 2 | 22 |
| 14 | 2 | NH | 2-pyridyl | 264 | 8.16(m,1H), 7.51(m,1H), 6.5–6.9(m,2H), 3.40(s,3H), 2.66(d,J=2,2H), 2.33(s,6H), 2.08(s,3H). | 2 | 25 |
| 15 | 2 | S | 2-pyrimidinyl | 282 | 8.70(d,J=5,2H), 7.01(t,J=5,1H), 3.46(s,3H), 2.81(s, 2H), 2.48(s,6H), 2.21(s,3H). | 2 | 25 |
| 16 | 2 | S | 2-(1-methyl)-imidazolyl | 300 | 6.8–7.1(m,2H), 3.6(s,3H), 3.3(s,3H), 2.65(d,J=2, 2H), 2.30(s,3H), 2.03(s,3H). | 2 | 37 |
| 17 | 2 | O | 5-chloro-2-pyridyl | 299, 301 | 8.21(d,J=2,1H), 7.48(d of d,J=8,J=2,1H), 6.66(d,J=8, 1H), 3.3(s,3H), 2.33(s,6H), 2.05(s,3H). | 2 | 27 |

EXAMPLE 18

Repetition of the procedures of Examples 1–3 but using the appropriate reactants of formulae III, IV, $H_2N$-$(CH_2)_n$-Z-R and R-Z-$(CH_2)_{n-1}$-CHO affords epimeric mixtures of the following compounds (Ac = acetyl; Pr = propionyl).

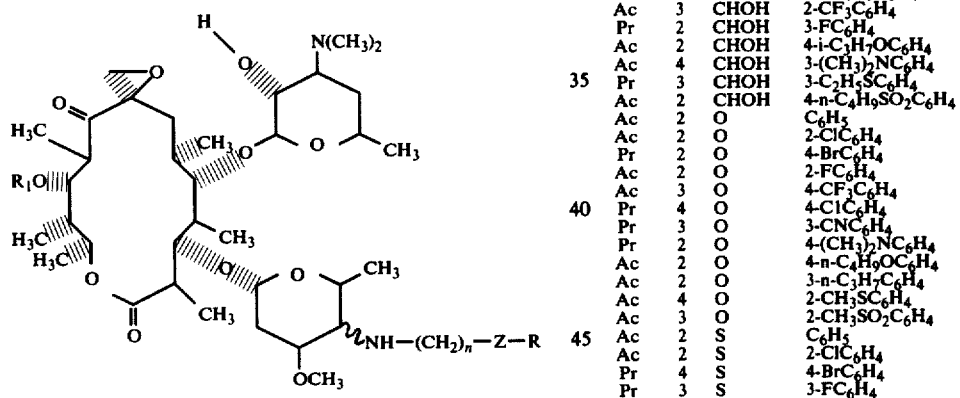

| $R_1$ | n | Z | R | Procedure |
|---|---|---|---|---|
| Pr | 2 | S | $C_6H_5$ | 2 |
| Pr | 2 | SO | $C_6H_5$ | 2 |
| Pr | 2 | $SO_2$ | $C_6H_5$ | 2 |
| Pr | 2 | O | $C_6H_5$ | 2 |
| Pr | 2 | NH | $C_6H_5$ | 1 |
| Pr | 1 | CHOH | $C_6H_5$ | 1 |
| Pr | 2 | CO | $C_6H_5$ | 2 |
| Pr | 1 | CO | $C_6H_5$ | 3 |
| Pr | 2 | S | 2-pyridyl | 2 |
| Pr | 2 | O | 2-pyridyl | 2 |
| Pr | 2 | S | 4-pyridyl | 2 |
| Pr | 2 | NH | 2-pyridyl | 2 |
| Pr | 2 | S | 2-pyrimidinyl | 2 |
| Pr | 2 | S | 2-(1-methyl)imidazolyl | 2 |
| Pr | 2 | O | 5-chloro-2-pyridyl | 2 |
| Ac | 1 | CO | 2-$ClC_6H_4$ | 3 |
| Ac | 3 | CO | 3-$BrC_6H_4$ | 2 |
| Ac | 1 | CO | 4-$FC_6H_4$ | 3 |
| Ac | 2 | CO | 2-$CH_3C_6H_4$ | 2 |
| Ac | 1 | CO | 4-$CH_3OC_6H_4$ | 3 |
| Ac | 1 | CO | 4-$CF_3C_6H_4$ | 3 |
| Ac | 1 | CO | 4-$(CH_3)_2NC_6H_4$ | 3 |
| Ac | 3 | CO | 2-$CNC_6H_4$ | 2 |
| Ac | 1 | CO | 3-$C_2H_5SC_6H_4$ | 3 |
| Ac | 1 | CO | 3-$C_2H_5SO_2C_6H_4$ | 3 |
| Ac | 4 | CO | $C_6H_5$ | 2 |
| Ac | 4 | CO | 4-$ClC_6H_4$ | 2 |
| Ac | 3 | CO | 4-$CH_3C_6H_4$ | 2 |
| Ac | 1 | CHOH | 3-$ClC_6H_4$ | 1 |
| Pr | 1 | CHOH | 4-$BrC_6H_4$ | 1 |
| Ac | 2 | CHOH | 4-$CNC_6H_4$ | 1 |
| Ac | 1 | CHOH | 4-t-$C_4H_9C_6H_4$ | 1 |
| Ac | 3 | CHOH | 2-$CF_3C_6H_4$ | 1 |
| Pr | 2 | CHOH | 3-$FC_6H_4$ | 1 |
| Ac | 2 | CHOH | 4-i-$C_3H_7OC_6H_4$ | 1 |
| Ac | 4 | CHOH | 3-$(CH_3)_2NC_6H_4$ | 1 |
| Pr | 3 | CHOH | 3-$C_2H_5SC_6H_4$ | 1 |
| Ac | 2 | CHOH | 4-n-$C_4H_9SO_2C_6H_4$ | 1 |
| Ac | 2 | O | $C_6H_5$ | 2 |
| Ac | 2 | O | 2-$ClC_6H_4$ | 2 |
| Pr | 2 | O | 4-$BrC_6H_4$ | 2 |
| Ac | 2 | O | 2-$FC_6H_4$ | 2 |
| Ac | 3 | O | 4-$CF_3C_6H_4$ | 2 |
| Pr | 4 | O | 4-$ClC_6H_4$ | 2 |
| Pr | 3 | O | 3-$CNC_6H_4$ | 2 |
| Pr | 2 | O | 4-$(CH_3)_2NC_6H_4$ | 2 |
| Ac | 2 | O | 4-n-$C_4H_9OC_6H_4$ | 2 |
| Ac | 2 | O | 3-n-$C_3H_7C_6H_4$ | 2 |
| Ac | 4 | O | 2-$CH_3SC_6H_4$ | 2 |
| Ac | 3 | O | 2-$CH_3SO_2C_6H_4$ | 2 |
| Ac | 2 | S | $C_6H_5$ | 2 |
| Ac | 2 | S | 2-$ClC_6H_4$ | 2 |
| Pr | 4 | S | 4-$BrC_6H_4$ | 2 |
| Pr | 3 | S | 3-$FC_6H_4$ | 2 |
| Ac | 2 | S | 4-$CH_3C_6H_4$ | 2 |
| Ac | 2 | S | 2-$C_2H_5OC_6H_4$ | 2 |
| Ac | 2 | S | 4-$CF_3C_6H_4$ | 2 |
| Ac | 2 | S | 3-$CH_3SO_2C_6H_4$ | 2 |
| Pr | 4 | S | 4-n-$C_4H_9SC_6H_4$ | 2 |
| Ac | 4 | S | 3-$CNC_6H_4$ | 2 |
| Ac | 4 | S | 4-t-$C_4H_9C_6H_4$ | 2 |
| Ac | 2 | S | 4-$ClC_6H_4$ | 2 |
| Pr | 4 | S | 4-$(CH_3)_2NC_6H_4$ | 2 |
| Ac | 2 | SO | $C_6H_5$ | 2 |
| Pr | 4 | SO | $C_6H_5$ | 2 |
| Ac | 2 | SO | 2-$ClC_6H_4$ | 2 |
| Pr | 4 | SO | 4-$BrC_6H_4$ | 2 |
| Pr | 3 | SO | 3-$FC_6H_4$ | 2 |
| Ac | 2 | SO | 4-$CH_3C_6H_4$ | 2 |
| Ac | 2 | SO | 2-$C_2H_5OC_6H_4$ | 2 |
| Ac | 2 | SO | 4-$CF_3C_6H_4$ | 2 |
| Ac | 2 | SO | 3-$CH_3SO_2C_6H_4$ | 2 |
| Ac | 4 | SO | 3-$CNC_6H_4$ | 2 |
| Pr | 4 | SO | 4-$(CH_3)_2NC_6H_4$ | 2 |
| Ac | 2 | $SO_2$ | $C_6H_5$ | 2 |
| Pr | 4 | $SO_2$ | $C_6H_5$ | 2 |
| Ac | 2 | $SO_2$ | 2-$ClC_6H_4$ | 2 |
| Pr | 4 | $SO_2$ | 4-$BrC_6H_4$ | 2 |
| Ac | 2 | $SO_2$ | 4-$CH_3C_6H_4$ | 2 |
| Ac | 2 | $SO_2$ | 4-$CF_3C_6H_4$ | 2 |
| Ac | 2 | $SO_2$ | 2-$C_2H_5OC_6H_4$ | 2 |
| Ac | 4 | $SO_2$ | 3-$CNC_6H_4$ | 2 |
| Pr | 4 | $SO_2$ | 4-$(CH_3)_2NC_6H_4$ | 2 |
| Ac | 4 | $SO_2$ | 4-n-$C_4H_9SC_6H_4$ | 2 |

-continued

| R₁ | n | Z | R | Procedure |
|---|---|---|---|---|
| Ac | 3 | NH | C₆H₅ | 1 |
| Pr | 2 | NH | 3-BrC₆H₄ | 1 |
| Ac | 4 | NH | 4-CH₃C₆H₄ | 1 |
| Pr | 2 | NH | 2-FC₆H₄ | 1 |
| Pr | 3 | NH | 3-C₂H₅OC₆H₄ | 1 |
| Ac | 4 | NH | 2-CF₃C₆H₄ | 1 |
| Ac | 2 | NH | 3-(CH₃)₂NHC₆H₄ | 1 |
| Ac | 2 | NH | C₆H₅ | 1 |
| Ac | 2 | NH | 3-C₂H₅SC₆H₄ | 1 |
| Ac | 3 | NH | 4-CF₃C₆H₄ | 1 |
| Pr | 4 | NH | 4-CNC₆H₄ | 1 |
| Pr | 3 | NH | 4-n-C₄H₉SC₆H₄ | 1 |
| Pr | 2 | NH | 4-C₂H₅SO₂C₆H₄ | 1 |
| Ac | 2 | S | 4-pyridyl | 2 |
| Pr | 3 | S | 4-pyridyl | 2 |
| Pr | 4 | S | 4-pyridyl | 2 |
| Pr | 2 | S | 2-pyridyl | 2 |
| Ac | 4 | S | 2-pyridyl | 2 |
| Ac | 2 | S | 3-pyridyl | 2 |
| Ac | 2 | SO | 4-pyridyl | 2 |
| Pr | 2 | SO | 4-pyridyl | 2 |
| Pr | 3 | SO | 4-pyridyl | 2 |
| Pr | 4 | SO | 4-pyridyl | 2 |
| Pr | 2 | SO | 2-pyridyl | 2 |
| Ac | 4 | SO | 2-pyridyl | 2 |
| Ac | 2 | SO | 3-pyridyl | 2 |
| Ac | 2 | SO₂ | 4-pyridyl | 2 |
| Pr | 2 | SO₂ | 4-pyridyl | 2 |
| Pr | 4 | SO₂ | 4-pyridyl | 2 |
| Ac | 2 | SO₂ | 2-pyridyl | 2 |
| Pr | 2 | O | 4-pyridyl | 2 |
| Ac | 2 | O | 4-pyridyl | 2 |
| Ac | 4 | O | 2-pyridyl | 2 |
| Pr | 2 | O | 3-pyridyl | 2 |
| Pr | 3 | O | 3-pyridyl | 2 |
| Ac | 2 | O | 2-pyridyl | 2 |
| Ac | 2 | O | 5-Cl-2-pyridyl | 2 |
| Pr | 4 | O | 5-Cl-2-pyridyl | 2 |
| Ac | 2 | O | 5-Cl-2-pyridyl | 2 |
| Ac | 2 | S | 5-Cl-2-pyridyl | 2 |
| Ac | 2 | SO | 5-Cl-2-pyridyl | 2 |
| Ac | 2 | SO₂ | 5-Cl-2-pyridyl | 2 |
| Pr | 4 | SO₂ | 5-Cl-2-pyridyl | 2 |
| Ac | 2 | NH | 4-pyridyl | 2 |
| Ac | 2 | NH | 2-pyridyl | 2 |
| Ac | 2 | NH | 3-pyridyl | 2 |
| Ac | 2 | NH | 4-pyridyl | 2 |
| Pr | 4 | NH | 3-pyridyl | 2 |
| Pr | 3 | NH | 2-pyridyl | 2 |
| Ac | 1 | CO | 4-pyridyl | 3 |
| Pr | 2 | CO | 3-pyridyl | 2 |
| Pr | 4 | CO | 3-pyridyl | 2 |
| Ac | 2 | CO | 2-pyridyl | 2 |
| Ac | 2 | CO | 5-Cl-2-pyridyl | 2 |
| Ac | 2 | CHOH | 4-pyridyl | 1 |
| Pr | 3 | CHOH | 2-pyridyl | 1 |
| Pr | 4 | CHOH | 4-pyridyl | 1 |
| Ac | 2 | CHOH | 2-pyrimidinyl | 1 |
| Ac | 4 | CHOH | 2-pyrimidinyl | 1 |
| Pr | 1 | CHOH | 2-pyrimidinyl | 1 |
| Ac | 1 | CO | 2-pyrimidinyl | 2 |
| Ac | 2 | CO | 2-pyrimidinyl | 2 |
| Pr | 4 | CO | 2-pyrimidinyl | 2 |
| Pr | 2 | O | 2-pyrimidinyl | 2 |
| Ac | 2 | O | 2-pyrimidinyl | 2 |
| Ac | 3 | O | 2-pyrimidinyl | 2 |
| Ac | 2 | S | 2-pyrimidinyl | 2 |
| Pr | 3 | S | 2-pyrimidinyl | 2 |
| Ac | 2 | SO | 2-pyrimidinyl | 2 |
| Pr | 3 | SO | 2-pyrimidinyl | 2 |
| Ac | 2 | SO | 2-pyrimidinyl | 2 |
| Ac | 2 | SO₂ | 2-pyrimidinyl | 2 |
| Pr | 3 | SO₂ | 2-pyrimidinyl | 2 |
| Ac | 4 | SO₂ | 2-pyrimidinyl | 2 |
| Pr | 2 | NH | 2-pyrimidinyl | 2 |
| Ac | 2 | NH | 2-pyrimidinyl | 2 |
| Pr | 3 | NH | 2-pyrimidinyl | 2 |
| Pr | 4 | NH | 2-pyrimidinyl | 2 |
| Ac | 4 | S | 2-(1-methyl)imidazolyl | 2 |
| Ac | 2 | SO | 2-(1-methyl)imidazolyl | 2 |
| Ac | 4 | SO | 2-(1-methyl)imidazolyl | 2 |
| Pr | 2 | SO₂ | 2-(1-methyl)imidazolyl | 2 |
| Pr | 2 | O | 2-(1-methyl)imidazolyl | 2 |
| Ac | 2 | O | 2-(1-methyl)imidazolyl | 2 |
| Ac | 4 | O | 2-(1-methyl)imidazolyl | 2 |
| Ac | 1 | CO | 2-(1-methyl)imidazolyl | 2 |
| Pr | 4 | CO | 2-(1-methyl)imidazolyl | 2 |
| Ac | 2 | CO | 2-(1-methyl)imidazolyl | 2 |
| Ac | 1 | CHOH | 2-(1-methyl)imidazolyl | 2 |
| Pr | 2 | CHOH | 2-(1-methyl)imidazolyl | 2 |
| Pr | 4 | CHOH | 2-(1-methyl)imidazolyl | 2 |
| Pr | 2 | NH | 2-(1-methyl)imidazolyl | 2 |
| Ac | 2 | NH | 2-(1-methyl)imidazolyl | 2 |
| Ac | 3 | NH | 2-(1-methyl)imidazolyl | 2 |
| Pr | 4 | NH | 2-(1-methyl)imidazolyl | 2 |

EXAMPLE 19

11,2'-Diacetyl-4"-deoxy-4"-[2-(4-pyridyl)thio ethyl]amino-oleandomycin

The procedure of Example 2 is repeated but using isopropanol as solvent in place of methanol to give the title product.

The 2'-acetyl group is solvolyzed as follows. A solution of the title compound (400 mg.) in methanol (20 ml.) is stirred at room temperature under an atmosphere of nitrogen for 18 hours. The solution is the evaporated to dryness under reduced pressure to give the 11-monoacetyl derivative.

EXAMPLE 20

11,2'-Diacetyl-4"-deoxy-4"-[2-(4-pyridyl)thio ethyl]amino-oleandomycin (by acetylation of 11-monoacetyl derivative)

Acetic anhydride (0.188 ml., 2.0 mmoles) is added to a solution of 11-monoacetyl-4"-deoxy-4"-[2-(4-pyridyl)thio ethyl]amino-oleandomycin (1.65 g., 2.0 mmoles) in benzene (15 ml.) under a nitrogen atmosphere at room temperature. The mixture is stirred for three hours and is then poured into water (25 ml.) layered with benzene (25 ml.). The pH is adjsuted to 9.5 with 6N NaOH and the benzene layer separated. It is washed successively with water and brine and then dried (Na₂SO₄) and concentrated under reduced pressure to a foam.

Similarly, the compounds of Examples 3-19 are converted to their corresponding 2'-acetyl derivatives and, by replacement of acetic anhydride with propionic anhydride, to their corresponding 2'-propionyl derivatives.

EXAMPLE 21

Acid Addition Salts

To a solution of 11-acetyl-4"-deoxy-4"-(2-phenylthio ethyl)amino-oleandomycin (1.0 mmole) in methanol (50 ml.) is added an equimolar proportion of hydrogen chloride and the reaction mixture stirred at room temperature for one hour. Removal of the solvent by evaporation affords the hydrochloride salt.

In like manner, the above-named compound and the remaining compounds described herein are converted to their hydrochloride, hydrobromide, sulfate, acetate, butyrate, citrate, glycolate, tartrate, stearate, pamoate, fumarate, benzoate and aspartate salts.

When the reactant is an 11,2'-dialkanoyl-4"-deoxy-4"-substituted amino-oleandomycin derivative, isopropanol is used as solvent.

Other acid addition salts are prepared by adding sufficient acid to satisfy each of the basic groups present. In this manner di- and tri-acid addition salts of compounds of this invention are prepared.

PREPARATION A 11,2'-Diacetyl-4"-deoxy-4"-oxo-oleandomycin

To 4.5 g. of N-chlorosuccinimide, 50 ml. of benzene and 150 ml. of toluene in a dry flask fitted with a magnetic stirrer and nitrogen inlet and cooled to −5° C. is added 3.36 ml. of dimethylsulfide. After stirring at 0° C. for 20 minutes, the contents are cooled to −25° C. and treated with 5.0 g. of 11,2'-diacetyl-oleandomycin in 100 ml. of toluene. Cooling and stirring are continued for 2 hours followed by the addition of 4.73 ml. of triethylamine. The reaction mixture is allowed to stir at 0° C. for 15 minutes, and is subsequently poured into 500 ml. of water. The pH is adjusted to 9.5 with 1N aqueous sodium hydroxide and the organic layer separated, washed with water and a brine solution and dried over sodium sulfate. Removal of the solvent in vacuo gives 4.9 g. of the desired product as a foam.

NMR (60 MHz) $\delta_{CDCl_3}^{TMS}$ (ppm): 3.48 (s, 3H), 2.61 (m, 2H), 2.23 (s, 2H), and 2.03 (s, 6H).

In like manner, the following 11,2'-dialkanoyl-4"-deoxy-4"-oxo-oleandomycins are prepared from the corresponding 11,2'-dialkanoyl-oleandomycins:

11,2'-dipropionyl-
11-acetyl-2'-propionyl-
11-propionyl-2'-acetyl

PREPARATION B

11-Acetyl-4"-deoxy-4"-oxo-oleandomycin

A solution of 4.0 g. of 11,2'-diacetyl-4"-deoxy-4"-oxo-oleandomycin in 75 ml. of methanol is allowed to stir at room temperature overnight. The reaction mixture is concentrated under reduced pressure to give the product as a foam. A diethyl ether solution of the residue, on treatment with hexane, gives 2.6 g. of the product as a white solid, m.p. 112°-117° C.

NMR (60 MHz) $\delta_{CDCl_3}^{TMS}$ (ppm): 3.43 (s, 3H), 2.60 (m, 2H), 2.23 (s, 6H), and 2.01 (s, 3H).

Following the above procedures, 11-propionyl-4"-deoxy-4"-oxo-oleandomycin is prepared from 11,2'-dipropionyl-4"-deoxy-4"-oxo-oleandomycin.

PREPARATION C

2'-Acetyl-4"-deoxy-4"-oxo-oleandomycin

Dimethylsulfide (0.337 ml.) is added to a turbid solution of 467 mg. of N-chlorosuccinimide in 20 ml. of toluene and 6 ml. of benzene cooled to −5° C. and maintained under a nitrogen atmosphere. After stirring at 0° C. for 20 minutes the mixture is cooled to −25° C. and 1.46 g. of 2'-acetyloleandomycin and 15 ml. of toluene are added. Stirring is continued for 2 hours at −20° C. followed by the addition of 0.46 ml. of triethyl amine. The reaction mixture is maintained at −20° C. for an additional 5 minutes and then allowed to warm to 0° C. The mixture is poured, with stirring, into 50 ml. of water and 50 ml. of ethyl acetate. The pH of the aqueous mixture is adjusted to 9.5 by addition of aqueous sodium hydroxide solution. The organic layer is subsequently separated, dried over sodium sulfate and concentrated in vacuo to a white foam (1.5 g.). Trituration with diethyl ether gives 864 mg. of crude product, which on recrystallization twice from methylene chloride-diethyl ether gives 212 mg. of the pure product, m.p. 183°-185.5° C.

Anal. Calc'd for $C_{37}H_{61}O_{13}N$: C, 61.1; H, 8.5; N, 1.9. Found: C, 60.9; H, 8.4; N, 1.9.

NMR (60 MHz) $\delta_{CDCl_3}^{TMS}$ (ppm): 5.60 (m, 1H), 3.50 (s, 3H), 2.73 (m, 2H), 2.23 (s, 6H) and 2.03 (s, 3H).

In like manner, 2'-propionyl-4"-deoxy-4"-oxo-oleandomycin is prepared from 2'-propionyloleandomycin.

PREPARATION D

4"-Deoxy-4"-oxo-oleandomycin

A solution of 1.0 g. of 2'-acetyl-4"-deoxy-4"-oxo-oleandomycin in 20 ml. of methanol is allowed to stir at room temperature overnight. The solution is concentrated in vacuo to give the desired product as a white foam, 937 mg.

NMR (60 MHz) $\delta_{CDCl_3}^{TMS}$ (ppm): 5.60 (m, 1H), 3.50 (s, 3H), 2.85 (m, 2H), and 2.26 (s, 6H).

Similarly, 2'-propionyl-4"-deoxy-4"-oxo-oleandomycin is hydrolyzed to 4"-deoxy-4"-oxo-oleandomycin.

PREPARATION E

11-Acetyl-4"-deoxy-4"-amino-oleandomycin

To a suspension of 10% palladium-on-charcoal (10 g.) in methanol (100 ml.) is added ammonium acetate (21.2 g.) and the resulting slurry is treated with a solution of 11-acetyl-4"-deoxy-4"-oxo-oleandomycin (20 g.) in 100 ml. of the same solvent. The suspension is shaken at room temperature in a hydrogen atmosphere at an initial pressure of 50 p.s.i. After 1.5 hours, the catalyst is filtered and the filtrate is added with stirring to a mixture of water (1200 ml.) and chloroform (500 ml.). The pH is adjusted from 6.4 to 4.5 and the organic layer is separated. The aqueous layer, after a further extraction with chloroform (500 ml.), is treated with ethyl acetate (500 ml.) and the pH adjusted to 9.5 with 1N sodium hydroxide. The ethyl acetate layer is separated and the aqueous layer extracted again with ethyl acetate. The ethyl acetate extracts are combined, dried over sodium sulfate and concentrated to a yellow foam (18.6 g.), which on crystallization from diisopropyl ether, provides 6.85 g. of the purified product, m.p. 157.5°-160° C.

NMR (δ, $CDCl_3$): 3.41 (3H)s, 2.70 (2H)m, 2.36 (6H)s and 2.10 (3H)s.

The other epimer, which exists in the crude foam to the extent of 20-25%, is obtained by gradual concentration and filtration of the mother liquors.

In like manner, the following mono-alkanoyl and dialkanoyl esters of 4"-deoxy-4"-amino-oleandomycin are prepared from the appropriate mono-alkanoyl and dialkanoyl 4"-deoxy-4"-oxo-oleandomycins. When a 2'-ester is prepared, isopropanol is used as solvent.

11,2'-diacetyl-
2'-acetyl-
2'-propionyl-
11,2'-dipropionyl-
11-propionyl-
11-acetyl-2'-propionyl-
11-propionyl-2'-acetyl-

PREPARATION F

4"-Deoxy-4"-amino-oleandomycin

A solution of 2'-acetyl-4"-deoxy-4"-oxo-oleandomycin (20 g.) in methanol (125 ml.), after stirring at room temperature overnight, is treated with ammonium acetate (21.2 g.). The resulting solution is cooled in an ice bath and treated with sodium cyanoborohydride (1.26 g.). The cooling bath is then removed and the reaction mixture allowed to stir at room temperature for 2 hours. The reaction is poured into water (600 ml.) and diethyl ether (600 ml.) and the pH adjusted from 8.3 to 7.5. The ether layer is separated and the aqueous phase extracted with ethyl acetate. The extracts are set aside and the pH of the aqueous adjusted to 8.25. The diethyl ether and ethyl acetate extracts made at this pH are also set aside, and the pH raised to 9.9. The diethyl ether and ethyl acetate extracts at this pH are combined, washed successively with water (1 X) and a saturated brine solution and dried over sodium sulfate. The latter extracts, taken at pH 9.9, are concentrated to a foam and chromatographed on silica gel (160 g.), using chloroform as the loading solvent and initial eluate. After eleven fractions, 12 ml. per fraction are taken, the eluate is changed to 5% methanol-95% chloroform. At fraction 370 the eluate is changed to 10% methanol-90% chloroform and at fraction 440, 15% methanol-85% chloroform is used. Fractions 85-260 are combined and concentrated in vacuo to dryness to provide 2.44 g. of the desired product.

NMR ($\delta$, CDCl$_3$): 5.56 (1H)m, 3.36 (3H)s, 2.9(2H)m and 2.26 (6H)s.

PREPARATION G

General Preparation of Aldehyde Reactants

To a slurry of sodium hydride (23.5 g. of 50%, 0.49 mole) in tetrahydrofuran is added a slurry of 4-mercaptopyridine (65.4 g., 0.5 mole) in tetrahydrofuran (400 ml.) and N,N-dimethylformamide (100 ml.) and the mixture stirred at room temperature for a half-hour. Bromoacetaldehyde diethyl acetal (98.6 g., 0.5 mole) in tetrahydrofuran (100 ml.) is then added over a five minute period and the resulting mixture stirred for 1.25 hour and then refluxed for one hour. The tetrahydrofuran is distilled off at atmospheric pressure, and the residue diluted with chloroform (200 ml.). It is washed successively with 1N NaOH, water and brine and then dried (Na$_2$SO$_4$). The dry solution is distilled to give the diethyl acetal of 2-(4-pyridyl)thio acetaldehyde (68.2 g., 71%), b.p. 140°-143° C. at 0.35 mm.

The diethyl acetal (27.3 g.) is dissolved in 5% hydrochloric acid (300 ml.) and stirred at room temperature for 18 hours. The reaction mixture is then freeze-dried to give a mixture of a solid and an oil. The solid is separated by filtration. NMR (D$_2$O) shows it to be the hydrate of 2-(4-pyridyl)thioacetaldehyde hydrochloride.

NMR (60 MHz) $\delta_{D_2O}^{TMS}$ (ppm): 7.6-8.6 (4H), 5.43 (t, J=5, 1H), 3.50 (d, J=5, 2H).

It is used directly in the reductive amination procedure of Example 2 without further purification.

PREPARATION H

General Procedure: Z = S → Z = SO Conversion

The thio aldehyde, e.g., 2-phenylthioacetaldehyde (1.1 g., 7.2 mmole) is dissolved in chloroform (8 ml.) and m-chloroperbenzoic acid (85%, 1.47 g., 7.2 mmole) in chloroform (12 ml.) is slowly added with stirring. The reaction mixture is stirred for 2.5 hours at room temperature, followed by one hour at 50° C. and then left at room temperature overnight. The reaction mixture is filtered and concentrated under reduced pressure to give the product as a white paste (2.5 g.).

NMR (60 MHz) $\delta_{CDCl_3}^{TMS}$ (ppm): 9.8 (t, J=2, 1H), 3.98 (d, J=2, 2H).

PREPARATION I

General Conversion of Z = S to Z = SO$_2$

The thio aldehyde, e.g., 2-phenylthioacetaldehyde (1.5 g., 9.8 mmole) is dissolved in chloroform (5 ml.) and a solution of m-chloroperbenzoic acid (85%, 4.0 g., 19 mmole) in chloroform (25 ml.) is slowly added with stirring. The reaction mixture is stirred overnight at room temperature and is then filtered and concentrated under reduced pressure to give 2.1 g. of a white paste which is used as is.

NMR (60 MHz) $\delta_{CDCl_3}^{TMS}$ (ppm): 9.8 (t, J=2, 1H), 4.13 (d, J=2, 2H).

PREPARATION J

General Procedure for R—CO—(CH$_2$)$_{n-1}$—CHO

Compounds having the above formula are prepared according to the procedure of Loozen, *J. Org. Chem.*, 40, 520-1 (1975) which comprises reaction of the appropriate aldehyde R-CHO with the appropriate Grignard reagent $$BrMg(CH_2)_{n-1}-CH\begin{smallmatrix}O\\O\end{smallmatrix}\Bigg\rangle,$$

to give an alcohol $$R-\underset{OH}{\underset{|}{CH}}-(CH_2)_{n-1}-CH\begin{smallmatrix}O\\O\end{smallmatrix}\Bigg\rangle,$$

which is then hydrolyzed to the corresponding hydroxyaldehyde or oxidized to the corresponding ketone and then hydrolyzed to a keto aldehyde by treatment with 5% HCl.

What is claimed is:

1. An epimeric compound having the formula and the pharmaceutically acceptable salts thereof wherein
each of R$_1$ and R$_2$ is selected from the group consisting of hydrogen, alkanoyl having from two to three carbon atoms and is selected from the group consisting of acetyl and propionyl;

n is an integer from 1 to 4;

Z is selected from the group consisting of O, S, SO, SO$_2$, CO, CHOH and NH; provided that when Z is O, S, SO, SO$_2$ or NH, n is an integer from 2 to 4 and when Z is CO or CHOH, n is an integer from 1 to 4;

and R is -heterocyclyl;

wherein heterocyclyl is selected from the group consisting of pyridyl, chloro substituted pyridyl, 2-pyrimidinyl and 2-(1-methyl)imidazolyl.

2. A compound according to claim 1 wherein $R_1$ is alkanoyl and $R_2$ is hydrogen.

3. A compound according to claim 2 wherein n is 2, and R is pyridyl.

4. A compound according to claim 2 wherein Z is S and R is 2-pyrimidinyl.

5. A compound according to claim 3 wherein Z is S and R is 2-pyridyl.

6. A compound according to claim 3 wherein Z is O and R is 2-pyridyl.

7. A compound according to claim 3 wherein Z is S and R if 4-pyridyl.

8. A compound according to claim 3 wherein Z is NH and R is 2-pyridyl.

* * * * *